United States Patent [19]

Cahalan et al.

[11] Patent Number: 4,605,406

[45] Date of Patent: Aug. 12, 1986

[54] METHOD FOR FABRICATING PROSTHESIS MATERIAL

[75] Inventors: Patrick T. Cahalan, Champlin; Carolann M. Holmblad, Cambridge; Robert W. Pike, Jr., Minneapolis; Eileen L. Schultz, Fridley, all of Minn.

[73] Assignee: Medtronic, Inc., Minneapolis, Minn.

[21] Appl. No.: 637,476

[22] Filed: Aug. 3, 1984

[51] Int. Cl.⁴ ................................................ A61F 1/24
[52] U.S. Cl. ......................................... 623/1; 521/64; 264/41; 523/114; 427/2
[58] Field of Search ........................... 521/64; 264/41; 523/114; 427/2; 623/1

[56]  References Cited
U.S. PATENT DOCUMENTS

| | | | |
|---|---|---|---|
| 4,173,689 | 10/1979 | Lyman et al. | 521/64 |
| 4,286,341 | 9/1981 | Greer et al. | 3/1 |
| 4,374,669 | 2/1983 | MacGregor | 3/1 |

OTHER PUBLICATIONS

"Biologic and Synthetic Vascular Prosthesis", James C. Stanley, M.D., published by Grund & Stratton, 1982.
"Structural Order and Blood Compatibility of Polymeric Prosthesis", IUPAC Molecular Symposium, Ciardelli, C. F. & Giusti, P., Eds. Pergammon Press, Ltd., Oxford, 1980, p. 205.
"An Elastomeric Vascular Prosthesis, vol. XXIV Trans. Am. Soc. Artif. Intern. Organs, 1978, p. 209.
"Blood-Materials Interactions—Twenty Years of Frustration", vol. XXVII, Trans. Am. Soc. Artif. Intern Organs, 1981, p. 659.
"Arterial Grafts", J. Cardiovas, Surg., 22, 1981, XV World Congress of the International Cardiovascular Society, pp. 515-518.

Primary Examiner—John Kight
Assistant Examiner—M. L. Moore
Attorney, Agent, or Firm—Vidas & Arrett

[57]  ABSTRACT

A method of fabricating prosthesis material having a conduit configuration.

21 Claims, No Drawings

METHOD FOR FABRICATING PROSTHESIS MATERIAL

BACKGROUND OF THE INVENTION

In general this invention relates to prosthesis material made of synthetic polymer. More specifically, it relates to an improved method for fabricating prosthesis material, particularly vascular, duct and other conduit material for use with living tissue.

Synthetic prosthesis material has long been the subject of intense investigative effort. The book "Biologic and Synthetic Vascular Prosthesis" edited by James C. Stanley, M.D., published by Grund & Stratton, 1982 provides a complete historic survey of this investigation. Dr. Stanley points out that various materials such as PTFE and polyurethane have been studied and tested. Most of the materials have been found unsatisfactory, particularly for vascular usage, due to the fact that the conduit structures formed of the materials have been, in the case of many materials thrombogenic and, in the cases of other materials such as PTFE, mechanically noncompliant particularly when used in small diameters. Moreover, porosity of the material has been found to be an important requirement which was not satisfactorily met by early materials.

A promising copolyurethane material developed by Lyman et al has been pointed out by Stanley. The Lyman et al material compares in porosity with knitted Dacron material. It is manfactured by liquid polymer precipitation on a mandrel to which an external mesh may be added for tensil strength. The material can be manufactured with varying compliance values by altering the wall density. More detailed information concerning the Lyman et al work is available in a paper by Lyman entitled "Structural Order and Blood Compatibility of Polymeric Prosthesis" which was printed in the IUPAC MACROMOLECULAR SYMPOSIUM, Ciardelli, C. F. & Giusti, P., Eds., Pergammon Press, Ltd., Oxford, 1980, at p. 205 and in the Lyman et al U.S. Pat. No. 4,173,689. The content of all references cited herein are incorporated by reference.

Polyurethane and copolyurethanes have been considered for prosthetic purposes as evidenced by an Annis et al article "An Elastomeric Vascular Prosthesis", Vol. XXIV Trans. Am. Soc. Artif. Intern. Organs, 1978, page 209; an article by Andrade et al entitled "Blood-Materials Interactions - Twenty Years of Frustration"; Volume XXVII, Trans. Am. Soc. Artif. Intern Organs, 1981 page 659 and a comment entitled "Experimental Study of a New Synthetic Vascular Graft" by Gruss et al which appeared at page 518 J. Cardiovas. Surg., 22, 1981 of the XV World Congress of the International Cardiovascular Society.

The synthetic polymer precipitation of these materials as first described by Lyman et al appears to offer the most satisfactory synthetic polymer prosthetic material to date. In that technique, sometimes referred to as a "Mandrel Coating Process" and as indicated above, the lumen of a tubular conduit is formed on a dipped mandrel. The characteristics of the material thus formed are subject to variation depending on the physical and chemical properties of the mandrel. Specifically, the surface characteristics of the mandrel determine in a large part the surface characteristics of the conduit lumen. Also, the wall thickness uniformity of the tubular conduit formed on a mandrel is dependent on selecting a polymer solution viscosity and a dip coating rate that allows film deposition over a significant length of mandrel without excessive running of the solution which results in uneven coating thickness. Furthermore, the polymer concentration is limited in that it is controlled by the type of pore structure desired in the coating.

In this particular technique, for a specific solution viscosity, the dip coating rate must be very exact to achieve a uniform coating on the mandrel. There is a narrow range of polymer solution viscosities which will coat a mandrel uniformly at any dip coating rate.

Although the Lyman et al technique as described in the aforementioned patent is related primarily to block copolymers and more specifically to copolyurethanes, it is generally applicable as is the present invention to any synthetic polymer which is amenable to the precipitation technique utilized. In the technique, a solvent appropriate for the particular synthetic polymer such as N, dimethylformamide for block copolyurethanes is utilized to form a solution of moderate viscosity. A forming device referred to herein as a mandrel or other tool of suitable surface configuration is slowly immersed in the viscous solution and then slowly withdrawn, leaving a solution coating on the mandrel comprising a uniform dispersion of polymer. Voids are introduced, i.e. porosity by extracting the polymer solvent into a miscible solvent in which the polymer is insoluble, resulting in precipitation of the polymer onto the mandrel.

The coated mandrel is exposed to the precipitating solution, which is usually water, by simply dipping the mandrel into it. The process of solvent displacement by the precipitating solution involves a concurrent transfer of precipitating solution into the spaces formerly occupied by the solvent molecules. When the precipitating solution is ultimately removed as by evaporation, the resulting cavities or voids within the polymer structure create a spongy texture, the desired elasticity of which may be matched to living tissue compliance requirements by control over the porosity. By repeating the dipping procedure, the thickness of the polymer coating can be increased and material compliance can be further adjusted to an altered elastic response, if desired.

Of the general class of block copolymers, copolyurethanes, particularly copolyurethane-ureas and copolyether-urethanes are representative of preferred synthetic polymer material for use with the invention and its objective which is the provision of improved synthetic prosthesis material particularly vascular prostheses having a lumen surface of improved smoothness for blood compatibility.

As indicated above, a problem is attendant with the Lyman et al technique wherein the polymer is precipitated on a mandrel in that the surface characteristics of the lumen, i.e. the interior surface of the synthetic vascular conduit material thus formed is determined as to its nature by the solid surface of the mandrel. This has been found to have a pronounced effect not only on its smoothness but on the porosity of the prosthesis material as well.

A pore gradient is also desirable for consistency and strength of the material. That is, it is desirable that the size of the pores should gradually increase through the wall thickness from about 1-2 microns to about 30 microns, for example, on the exterior of the wall to encourage tissue ingrowth. This is not readily obtained by the Lyman et al technique and resort has been taken to multi-coated layers to obtain desired pore size and pore distribution throughout the wall thickness.

On the other hand, this invention provides an improved precipitation technique making possible the formation of improved lumen surface smoothness and desired porosity and in which multi-coated layer formation is not necessary to obtain various wall thicknesses with desired pore size and pore distribution and mechanical compliance.

SUMMARY AND OBJECTIVES OF THE INVENTION

It is therefore a general object of the present invention to provide an improved method of forming synthetic polymer prostheses material by polymer precipitation.

It is also an object of the invention to provide a synthetic material and a method of making same, the material having mechanical compliance closely matched with body tissue, desirable pore size, pore gradation and pore distribution by means of simplified method steps.

It is also an object of the invention to provide synthetic material particularly adapted for vascular prostheses relating to the provision of channels or conduits for the conveyance of body fluids such as blood in veins and arteries, bile in ducts and urine in a urethra; and the like.

It is also an object of the invention to provide compliant small diameter synthetic polymer prostheses particularly those less than six millimeters in ID.

In general, the objectives of the invention are attained by forming a surface of the synthetic polymer material at a liquid-liquid interface as opposed to the prior art precipitation technique in which the surface of the material was formed at a liquid-solid interface. Additionally, special additives may be included in the polymer solution for additional porosity control as desired.

The method of the invention involves fabrication of a synthetic material by precipitation of a synthetic polymer from a solution onto the inside wall of a tube or other cylindrical conduit, the precipitation being carried out in the presence of a precipitating solution which provides a liquid-liquid interface for the formation of the inner surface of the synthetic material. In the case of the formation of tubular conduit material such as vascular conduits and the like, precipitation of the polymer against the inside wall of a tube provides a prosthesis having a lumen of improved smoothness and desirable pore characteristics along with more uniform dimensions. The lumen is formed at the interface established by the polymer solvent and the non-solvent or precipitating solution. SEM analysis has shown this surface to be smoother than surfaces deposited on the solid surface of a mandrel. Wall thickness can be controlled and varied by using a wide range of polymer solution viscosities.

DETAILED DESCRIPTION

The invention will be described in detail with reference to the formation of vascular prostheses, i.e. in tubular conduit form with a lumen of improved smoothness. Two embodiments of the method will be described.

In the first embodiment a vascular prostheses is formed by precipitation of a polymer from a solution by solvent extraction using a non-solvent or precipitating solution for the specific polymer involved. In accordance with the method the polymer solution fills a tube and the precipitation is effected by creating a void space in the column of polymer solution in the tube. The polymer solvent is extracted by causing the void space to move along the tube through the column of polymer solution and following it with the precipitating solution whereby the polymer precipitates against the interior wall of the tube forming a coating thereon with a smooth lumen formed at a liquid-liquid interface. The uniformity of the wall thickness is maintained by the fact that the column of polymer solution is contained within a tube of uniform dimension and the lumen size may be controlled by the movement of a uniform bubble or void space followed by the precipitating solution which effects precipitation of the polymer against the interior wall of the tube. This particular manner for precipitation creates a tubular conduit or vascular form the dimensions of which are dictated by the tube dimensions and the polymer viscosity. Long, uniformly dimensioned vascular prostheses of precipitated polymer may be formed utilizing this method. SEM analysis, mechanical testing and dimensional analysis have confirmed the uniformity of the tubular conduit. In particular, SEM analysis of the lumen surface has shown that surface to be very smooth, a desirable characteristic for blood compatibility.

In the second embodiment of the method of this invention, the polymer solution is again introduced into a tube. The tube is either filled or the polymer solution is allowed to flow over the interior surface and distribute itself evenly over the interior wall of the tube as by rocking the tube or otherwise tipping, tilting and rotating it. The excess is poured from the tube and the tube is then filled with the precipitating solution as by merely immersing the tube, within a bath thereof to cause the extraction and precipitation action which forms the prosthesis material on the interior wall of the tube. Again, since the lumen is formed at a liquid-liquid interface, improved smoothness results.

In both methods, the variabilities of wall thickness and porosity may pe controlled by controlling the viscosity of the polymer solution and the speed of extraction. Additionally, the amount and size of the porosifier, i.e. the porosity additive described hereinbelow may also be utilized to control these variables.

As already indicated above, any polymer capable of being solution precipitated may be utilized for the method of this invention. Of course, the polymer must be a blood compatible polymer which is not thrombogenic. For example, elastomers such as polyurethane-urea both the ester and ether type (a commercial form known as Biomer is available from ETHICON, Inc., Somerville, N.J., ethylene vinyl acetate such as Elvax ®, (available from E. I. DuPont de Nemours Co.), polyesterurethane and polyetherurethane, and Kraton ®, a styrene-butadiene elastomer available from Shell Chemical Co., Houston, Tex. The polyurethanes and copolyurethanes are the most preferred polymer such as Estane ® 5701 or 5714 available from B. F. Goodrich Chemical Co. of Cleveland, Ohio.

As already indicated the polymer starting material is dissolved in a suitable non-adverse solvent of the dipolar aprotic type. Examples are dimethylacetamide (DMAC), dioxane, dimethyl formamide (DMF), dimethyl sulfoxide (DMSO) and tetrahydrofuran (THF). Generally speaking, solvents of the sulfoxide or amide type are preferred. The amount of solvent used is adjusted to yield a resulting solution having a desired viscosity, which is dependent on the wall thickness desired. DMAC is the most preferred solvent for use with the urethanes.

The most preferred precipitating solution or extraction solvent is water which is preferably of the dionized type. However, mixtures of water and DMAC and water with ethyl alcohol have also been found to function as a precipitating solution. The water/DMAC mixture may be about 25% DMAC and the water ethanol mixture may be about 50–75% ethanol.

Additives, also referred herein as porosifiers, may be used to increase control over porosity of the prosthetic material. These additives may be placed directly in the polymer solution and include for example methyl cellulose, such as Methocel ®, hydroxypropyl methyl cellulose, available from the Dow Chemical Co., Midland, Mich., polyvinyl pyrrolidone (PVP), polyvinyl alcohol, silica (hydrophylic silica), sodium citrate and other such products which are water soluble and extractable.

The porosity of the prosthetic material can be adjusted as desired by having more or less of these porosifiers to provide controlled porosity distribution. The porosifier occupies space in the polymer and leaves voids when extracted by the precipitating solution. This controlled porosity avoids weak spots in the material which, in the case of vascular prosthesis can be a source of concern with respect to possible bursting. Porosity of the prosthetic material is also important for ingrowth of body tissue and mechanical compliance of the material.

The material of the tube within which the prosthetic material of the invention is formed may be of a wide variety of materials, Teflon, glass, polypropylene, silicone and stainless steel are examples of satisfactory materials which provide a satisfactory tube for use with the method. The tube may be rigid or flexible.

Based on the total weight of the solution, the polymer and solvent may vary in amount over a wide range. Typically, the solution will consist of 2–20% by weight of the polymer depending on the molecular weight of the polymer, the solvent making up the balance. If porosifier additives are used, they may range up to as much as 4% by weight of the total solution. If the solvent comprises less than about 80% of the solution, its viscosity is usually too high for convenient handling and if it comprises more than about 98% of the solution there is too little polymer present to obtain satisfactory prosthesis material since the material tends to be much too porous at such low amounts of polymer.

In the case of vascular prostheses, any of the aforementioned polyurethanes are most preferably utilized in an amount by weight of the total solution of about 10% with a solvent comprised of 84.5% DMAC and 5% THF by weight of the total solution and further including 0.5% Methocel as a porosifier additive. The preferred precipitating solution in this instance is water.

In the first procedure for practicing the method of the invention, a tube such as a glass tube is filled with polymer solution. One end of the glass tube is attached to a pump or source of vacuum while the other end of the tube is immersed in a reservoir of precipitating solution, the tube being stood upright therein. Application of a vacuum or pumping action at the upper end of the glass tube, forms a bubble or void space at the lower end of the polymer solution column in the tube. The bubble is caused to move upwardly within the column by the continued action by the pump or vacuum. As it moves upwardly, it is followed by the precipitating solution from the bath reservoir which moves upwardly through the column also. The retraction of the polymer solution from the tube with the bubble or void space leaves a coating of the polymer solution on the internal wall of the glass tube which is contacted by the precipitating solution whereby the polymer precipitates against the inside wall of the tube in the form of a tubular conduit or vascular prosthesis the lumen of which is formed at a liquid-liquid interface. For rinsing, the prosthesis may be removed from the tube by simply pulling it loose.

The two examples which follow were utilized with this procedure to produce vascular prostheses. As above, the percentages specified in all subsequent examples refer to the percent by weight of total solution.

EXAMPLE 17.8% of Pellethane 80A was dissolved in DMAC. The precipitating solution was 65% DMAC balance water. The precipitating solution was circulated through a glass tube as described above for about 20 minutes followed by an 18 hour circulation of water only.

A vascular prostheses was formed within the glass tube having an OD of 0.236 inches, an ID of 0.193 inches and a wall thickness of 0.0196 inches.

EXAMPLE

An 18% solution of Pellethane 80A was dissolved in DMAC. The precipitating solution was composed of 75% DMAC, balance water. The precipitating solution was circulated through the glass tube to form the vascular prosthesis therein for about 10 minutes followed by an 18-hour circulation of water only. Again, the vascular prosthesis thus formed was of the same basic dimensions as mentioned above for the preceding example.

In each case, the vascular prosthesis is readily removed from the interior of the glass tube by merely pulling it loose.

The second procedure which may be utilized with the method of the invention is the most preferred technique since it tends to be faster. In this technique, the polymer solution is included within a tube, such as a glass tube, as before. For convenience, the tube may be filled with polymer solution and then poured out leaving a liquid layer coated on the interior surface thereof. The tube may then be rocked gently in order to evenly distribute the liquid coating on the interior wall thereof. Then the tube is merely immersed within a bath of the precipitating solution and allowed to remain there for an adequate amount of time within which to effect precipitation of the polymer onto the internal wall of the tube to form the vascular prosthesis. Typically, 18–24 hours of immersion are required following which the prosthesis may be merely pulled from the tube.

The following examples were prepared by this second procedure.

EXAMPLE

18% of an aliphatic polyuretherurethane marketed by Thermoelectric Corporation of Waltham, Massachusetts as Tecoflex ® was dissolved in DMAC. The precipitating solution was water only. The coated glass tube was immersed in a water reservoir for 18 hours with 4 changes of the water bath.

EXAMPLE

A solution containing 18% of Pellethane 80A was dissolved in DMAC with 1% of PVP as a porosifier additive. The precipitating solution was water.

EXAMPLE

A solution containing 18% of Pellethane 80A was dissolved in DMAC with 1% of PVP as a porosifier additive. The precipitating solution was 27% ethanol balance water.

EXAMPLE

A solution containing 18% of Pellethane 80A was dissolved in DMAC with 1% of PVP as a porosifier additive. The precipitating solution was 50% ethanol balance water.

EXAMPLE

A solution containing 18% of Pellethane 80A was dissolved in DMAC with 1% of PVP as a porosifier additive. The precipitating solution was 100% ethanol.

EXAMPLE

A solution containing 18% of Tecoflex ® polyetherurethane was dissolved in DMAC with 1% PVP. The precipitating solution was water only.

EXAMPLE

A solution containing 18% of Tecoflex ® polyetherurethane was dissolved in DMAC with 1% PVP. The precipitating solution was 27% ethanol balance water.

EXAMPLE

A solution containing 18% of Tecoflex ® was dissolved in DMAC with 1% PVP. The precipitating solution was 50% ethanol balance water.

EXAMPLE

A solution containing 18% of Tecoflex ® was dissolved in DMAC with 1% PVP. The precipitating solution was 100% ethanol.

EXAMPLE

A solution containing 18% of Pellethane 80A was dissolved in DMAC with 1% silica. The precipitating solution was water.

EXAMPLE

A solution containing 18% of Pellethane 80A was dissolved in DMAC with 2% PVP. The precipitating solution was water.

EXAMPLE

A solution containing 9% Pellethane 80A was dissolved in DMAC with 1% Methocel. The precipitating solution was water.

EXAMPLE

A solution containing 9% Pellethane 80A was dissolved in DMAC with 0.5% Methocel ® hydroxypropyl methyl cellulose. The precipitating solution was water.

EXAMPLE

A solution containing 9% Pellethane 80A was dissolved in 80% DMAC/10% THF with 0.5% Methocel ® hydroxypropyl methyl cellulose. The precipitating solution was water.

EXAMPLE

A solution containing 9% Pellethane 80A was dissolved and 85% DMAC/5% THF solution with 0.5% Methocel ® hydroxypropyl methyl cellulose. The precipitating solution was water.

All of the above examples provided vascular prostheses having a 4 mm ID and 0.6 mm wall thickness with a substantially improved ultra-smooth lumen surface after about eighteen hours in the bath.

The surface chemistry of the lumen surface of these prostheses as tested by ESCA analysis showed it to be enriched in ether functionalities which is believed to be responsible, along with the ultra-smoothness, for improved blood compatibility of the prosthetic material made according to this invention.

Their pore size, based on SEM data, ranged from about 5-10 microns on the lumen surface of the prosthetic to about 50 microns on the outer wall thereof.

The porosity of the various prostheses made and described in the above examples was monitored by measuring the water permeability of the walls thereof at 80 mm of Hg and ranged from about 26 milliliters per minute per square centimeter to about 77 millimeters per minute per square centimeter. The range of porosity is believed to be dependent on the ratios of the stated compositions.

An advantage of the method of the invention is that vascular prostheses of various wall thicknesses can be made in one step rather than with the multi-coat layer technique utilized with the mandrel as in the Lyman et al procedure. However, a multiple coat technique may also be utilized in accordance with the present invention if desired. Such a procedure may be utilized to vary porosity, thickness and even composition of various portions of the wall by forming the prosthesis in multiple layers which involve filling the tube with one polymer solution then draining it and refilling the tube with another polymer solution and so forth. After draining the last polymer solution from the tube, the extraction process or precipitation process can be carried out as previously described.

EXAMPLE

First fill: A 10% solution of Pellethane 80A was dissolved in 89.5% DMAC with 0.5% Methocel was prepared.

Second fill: A 9.5% Pellethane 80A solution in 45% DMAC and 45% THF with 0.5% Methocel was utilized.

After draining out the second filling solution, the polymer was precipitated with water. The resulting vascular prosthesis had a thicker region of small pores near the lumen surface thereof than that found in prostheses extracted after the first fill only. Such an arrangement improves the strength of the prosthesis as well as providing the ultra-smooth lumen surface.

Another advantage of such a procedure is that, when different polymers are used for layering, composites may be formed such as a vascular prosthesis having an exterior of polyester urethane and an interior of polyetherurethane.

Having described the invention, the exclusive property rights to which applicants are entitled are defined in the following claims.

What is claimed is:

1. A method of fabricating a prosthesis material for use with a living body, the prosthesis material having a surface of improved smoothness, the method comprising the steps of:
   (a) coating the interior surface of a tube with a solution comprised of a synthetic polymer, having suitable compatibility characteristics, dissolved in a solvent, and (b) precipitating the polymer as a coating on the interior surface of the tube by contacting the polymer solution with a precipating solution comprised of a fluid which is miscible with the solvent but operable as a precipitating nonsolvent with respect to the polymer.

2. A method of fabricating a vascular prosthesis for use in a living body, the prosthesis having a lumen surface of improved smoothness, the method comprising the steps of:

(a) filling a length of tubing with a solution comprised of a synthetic polymer, having suitable compatability characteristics, dissolved in a solvent, (b) forming a space in the solution at an end of the tube whereby the wall of the tube around the space is covered with a remaining amount of the solution, (c) causing the space to move along the length of the tube, and (d) introducing a quantity of a precipitating solution into the tube behind the moving space to fill the void formed in the tube by the moving space and to contact the polymer solution coating the interior surface of the tube, the precipitating solution being comprised of a fluid which is miscible with the solvent but operable as a precipitating nonsolvent with respect to the polymer, and (e) whereby the polymer is caused to form a continuous solid coating within the tube.

3. The method of claim 2 including the additional step of removing the coating from the tube as a length of vessel.

4. A method of fabricating a vascular prosthesis for use in a living body, the prosthesis having a lumen surface of improved smoothness, the method comprising the steps of:

(a) forming a liquid layer on the interior surface of a tube, the layer comprising a solution of a polymer dissolved in a solvent, the polymer having suitable compatability characteristics as a prosthesis; and (b) contacting the liquid layer with a precipitating solution to precipitate the polymer onto the interim surface of the tube.

5. The method of claim 4 wherein the precipitating solution is introduced into the tube by immersing the tube in a bath of the precipitating solution.

6. The method of claim 4 wherein the tube is filled with the precipitating solution.

7. The method of either claims 1, 2 or 4 wherein the synthetic polymer is a block copolymer.

8. The method of either claims 1, 2 or 4 wherein the synthetic polymer is a polyurethane.

9. The method of either claims 1, 2 or 4 wherein the synthetic polymer is a copolymer.

10. The method of claim 9 wherein the copolymer is a copolymer-urethane.

11. The method of claim 9 wherein the copolymer is a copolymer-urethane urea.

12. The method of either claims 1, 2 or 4 wherein the solvent is selected from the group consisting of sulfoxide solvents and amide solvents.

13. The method of claim 12 wherein the solvent is selected from the group consisting of dimethyl foramide and dimethyl acetamide.

14. The method of either claims 1, 2 or 4 wherein the precipitating nonsolvent is water.

15. A blood and tissue compatible synthetic prosthesis prepared in accordance with the method defined in either claims 1, 2 or 4 wherein the material has mechanical properties of compliance and elasticity approximating those of organic tissue.

16. A prosthesis duct formed in accordance with either claims 1, 2 or 4.

17. A vascular graft formed in accordance with the method defined in either claims 1, 2 or 4.

18. The method of either claims 1, 2 or 4 wherein an additive is included in the polymer solution to aid in control over the porosity of the material.

19. The method of claim 18 wherein the additive is selected from the group consisting of hydroxypropyl methylcellulose, polyvinylpyrollidone, sodium citrate and silica.

20. A method of fabricating a prosthesis conduit material for use with a living body, the prosthesis material having a lumen surface of improved smoothness, the method comprising the steps of:

(a) providing a support element having a conduit therethrough;

(b) providing the interior surface of the support element conduit with a quantity of a solution comprised of a synthetic polymer, having suitable compatibility characteristics, dissolved in a solvent, and (c) precipitating the polymer as a coating at the interior surface of the support element and at a liquid-liquid interface by contacting the polymer solution with a precipitating solution comprised of a fluid which is miscible with the solvent but operable as a precipitating nonsolvent with respect to the polymer whereby prosthesis conduit material is formed against the support conduit interior surface.

21. The method of claim 20 wherein the material is removed from the support element.

* * * * *